(12) United States Patent
Takarada et al.

(10) Patent No.: US 7,659,060 B2
(45) Date of Patent: Feb. 9, 2010

(54) METHOD FOR IDENTIFYING NUCLEOTIDE POLYMORPHISM

(75) Inventors: Yutaka Takarada, Tsuruga (JP); Yoshihiro Soya, Tsuruga (JP); Yoshihisa Kawamura, Tsuruga (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 357 days.

(21) Appl. No.: 10/653,586

(22) Filed: Sep. 2, 2003

(65) Prior Publication Data
US 2004/0081991 A1 Apr. 29, 2004

(30) Foreign Application Priority Data
Sep. 2, 2002 (JP) .............................. 2002-256955

(51) Int. Cl.
*C12Q 1/68* (2006.01)
*C12P 19/34* (2006.01)

(52) U.S. Cl. .......................................... 435/6; 435/91.2
(58) Field of Classification Search ....................... None
See application file for complete search history.

(56) References Cited

U.S. PATENT DOCUMENTS 5,571,673 A * 11/1996 Picone ........................... 435/6
5,827,653 A 10/1998 Sammes et al.
2001/0041334 A1* 11/2001 Rashtchian et al. ............ 435/6

FOREIGN PATENT DOCUMENTS

| EP | 0 699 768 A1 | 3/1996 |
|---|---|---|
| WO | WO 98/18965 A1 | 5/1998 |
| WO | WO 99/28500 A1 | 6/1999 |

OTHER PUBLICATIONS

Nauck et al (1999), "Rapid, homogeneous genotyping of the 4G/5G polymorphism in the promoter region of the PAII gene by fluorescence resonance energy transfer and probe melting curves", Clinical Chemistry, vol. 48, No. 8, pp. 1141-1147.*
De Silva D et al 'Rapid genotyping and quantification on the LightCycler with hybridization probes' Biochemica (1998) No. 2, pp. 12-15.*
Lobashevsky AL et al 'Allele-specific in situ analysis of microchimerism by fluorescence resonance energy transfer (FRET) in nonhuman primate tissues.' Hum Immunol. Feb. 2002;63(2):108-20.*
Jobs M. et al. 'DASH-2: Flexible, Low-Cost, and High-Throughput SNP Genotyping by Dynamic Allele-Specific Hybridization on Membrane Arrays' Genome Research (2003) vol. 13, pp. 916-924.*
Heller et al., "Chemiluminescent and Fluorescent Probes for DNA Hybridization Systems," in *Rapid Detection and Identification of Infectious Agents*, Kingsbury and Falkow, editors, Academic Press Inc. (1985), pp. 245-256.
Cardullo et al., "Detection of nucleic acid hybridization by nonradiative fluorescence resonance energy transfer," *Proc. Natl. Acad. Sci. USA*, 85, 8790-8794 (1988).
Morrison, "Detection of Energy Transfer and Fluorescence Quenching" (Chapter 13), in *Nonisotopic DNA Probe Techniques*, Academic Press Inc. (1992), pp. 311-352.
Cane et al., "Use of Real-Time PCR and Fluorimetry To Detect Lamivudine Resistance-Associated Mutations in Hepatitis B Virus," *Antimicrobial Agents and Chemotherapy*, 43 (7), 1600-1608 (1999).
Howell et al., "iFRET: An Improved Fluorescence System for DNA-Melting Analysis," *Genome Research*, 12, 1401-1407 (2002).
Cantor, "Lighting up hybridization," *Nature Biotechnology, Nature Publishing*, 14, 247 (1996).
Gundry et al., "Rapid *F508del* and *F508C* Assay Using Fluorescent Hybridization Probes," *Genetic Testing*, 3 (4), 365-370 (1999).
Tyagi et al., "Molecular Beacons: Probes that Fluoresce upon Hybridization," *Nature Biotechnology*, 14, 303-308 (1996).
Wittwer et al., "Continuous Fluorescence Monitoring of Rapid Cycle DNA Amplification," *BioTechniques*, 22 (1), 130-131, 134-138 (1997).

\* cited by examiner

*Primary Examiner*—Stephen Kapushoc
(74) *Attorney, Agent, or Firm*—Leydig, Voit & Mayer, Ltd.

(57) ABSTRACT

A method for identifying a nucleotide polymorphism, the method comprising hybridizing a labeled oligonucleotide for a wild type or a mutant type to a nucleic acid containing a specific nucleotide polymorphic site in a sample; allowing a nucleic acid-specific label to act thereon; detecting an interaction between the label of the oligonucleotide and the nucleic acid-specific label; and identifying a nucleotide polymorphism, wherein the identification utilizes a difference due to the nucleotide polymorphism in conditions under which the hybridized oligonucleotide is separated into a single strand.

7 Claims, 3 Drawing Sheets

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial
<220> FEATURE:
<223> OTHER INFORMATION: A synthetic DNA having a sequence containing a
      nucleotide polymorphic site (Glu298Asp) of the human endothelial
      nitric oxide synthase gene.

<400> SEQUENCE: 1
cccagatgag cccccagaac                                                20

<210> SEQ ID NO 2
<211> LENGTH: 19
<212> TYPE: DNA
<213> ORGANISM: Artificial
<220> FEATURE:
<223> OTHER INFORMATION: A synthetic DNA having a sequence of the human
      endothelial nitric oxide synthase gene.

<400> SEQUENCE: 2
acggtcgctt cgacgtgct                                                 19
```

```
<210> SEQ ID NO 3
<211> LENGTH: 19
<212> TYPE: DNA
<213> ORGANISM: Artificial
<220> FEATURE:
<223> OTHER INFORMATION: A synthetic DNA having a sequence complementary
      to the human endothelial nitric oxide synthase gene.

<400> SEQUENCE: 3
gcacctcaag gaccagctc                                                    19
```

METHOD FOR IDENTIFYING NUCLEOTIDE POLYMORPHISM

BACKGROUND OF THE INVENTION

1. Field of the Invention

The present invention relates to a method for identifying a mutation or a polymorphism in a nucleic acid sequence. The present invention is particularly useful for diagnoses of genetic diseases, analyses of nucleotide polymorphisms and the like.

2. Description of Related Art

As used herein, a nucleotide polymorphism refers to a difference in a nucleotide sequence from a wild type. It is known that nucleotide polymorphisms of genes play important roles in drug metabolism as causal factors of variation among individuals in side effects or unsuccessful therapies. They are also known as causal factors of individual differences known as constitutions such as basal metabolism. In addition, nucleotide polymorphisms serve as genetic markers for a number of diseases. Therefore, it is clinically important to elucidate such mutations. Routine phenotypic classification is particularly recommended for psychiatric patients and suicidal patients in clinical studies (Gram and Brsen, European Consensus Conference on Pharmacogenetics. Commission of the European Communities, Luxembourg, pp. 87-96 (1990); Balant et al., Eur. J. Clin. Pharmacol., 36:551-554 (1989)). A method for analyzing a nucleic acid sequence is desired for detection of genotypes following identification of a responsible mutant type gene.

A nucleic acid sequence determination method (a sequencing method) exemplifies a conventional nucleic acid sequence analysis technique. A sequencing method may be used to detect and identify a nucleotide polymorphism contained in a nucleic acid sequence. However, it requires a great deal of labor and time for preparation of a template nucleic acid, a DNA polymerase reaction, polyacrylamide gel electrophoresis, analysis of a nucleic acid sequence and the like. The labor may be saved by using a recent automated sequencer, although the necessary equipment is expensive.

On the other hand, various genetic diseases are known to be caused by point mutations in genes. For some of them, the sites and types of point mutations in the genes that cause the genetic diseases are known.

A method for detecting a point mutation in a gene utilizing a gene amplification method such as the Polymerase Chain Reaction (PCR) method (JP-B 4-67960; JP-B 4-67957) is conventionally known as a method for detecting such an expected point mutation. An oligonucleotide for a wild type which is completely complementary to a terminal portion of a region to be amplified in a wild type gene, and an oligonucleotide for a mutant type which is completely complementary to a terminal portion of a region to be amplified in a mutant type gene are used as one of paired oligonucleotides for gene amplification in this method. The oligonucleotide for a mutant type has a nucleotide complementary to the nucleotide responsible for the expected point mutation at its 3' end. A gene in a sample is subjected to a gene amplification method using such oligonucleotides for a wild type and a mutant type independently.

If a gene in a sample is a wild type, nucleic acid amplification occurs using an oligonucleotide for a wild type. However, an extension reaction does not occur and, therefore, the nucleic acid amplification does not occur using an oligonucleotide for a mutant type because the 3' end of the oligonucleotide is not complementary to (is mismatched with) the corresponding nucleotide in the gene in the sample. On the other hand, if a gene in a sample is a mutant type, amplification does not occur using an oligonucleotide for a wild type, whereas the amplification occurs using an oligonucleotide for a mutant type. Thus, it is possible to determine whether a gene in a sample is a wild type or a mutant type by examining whether or not amplification occurs using one of the oligonucleotides, thereby identifying a point mutation in the gene in the sample. In this case, the presence of an amplified nucleic acid can be detected to examine the occurrence of amplification by electrophoresis of an amplification product on agarose gel, staining the agarose gel with a fluorescent reagent that specifically binds to nucleic acids (e.g., ethidium bromide) and UV irradiation. Alternatively, a Southern blotting method in which an amplified nucleic acid is immobilized on a nylon membrane and detection is carried out using a labeled probe; a sandwich hybridization method in which an amplified nucleic acid is captured by a capture probe immobilized on a solid substrate and a detection probe is then allowed to act thereon for detection; and the like have been developed.

Instead of direct detection of a fluorescence intensity, the Fluorescence Resonance Energy Transfer (FRET) method is utilized for detection of hybridization with a probe according to a recently developed detection method. Fluorescence resonance energy transfer is generated between a donor fluorescent substance and a quencher dye (which may be or may not be a fluorescent substance). It is generated if the absorption spectrum for one (a quencher) overlaps with the emission spectrum for another (a donor), and the two dyes are located in close proximity. A pair of dyes having such properties are called a donor/quencher dye pair or an energy transfer dye pair.

Excitation energy of a donor fluorescent substance is transferred to an adjacent quencher due to a dipolar interaction caused by a resonant dipole, resulting in quenching of the donor fluorescent substance. In some cases, if the quencher is also a fluorescent substance, the fluorescence intensity may be enhanced. An energy transfer efficiency highly depends on the distance between the donor and the quencher. An equation for estimating the relationship was developed by Forster (Forster, T., Ann. Phys., 2:55-75 (1948)). A distance between a donor and a quencher dye that results in an energy transfer efficiency of 50% is called a Forster distance (Ro). For example, other modes of fluorescence quenching include charge transfer quenching and collisional quenching.

Energy transfer and other modes based on quenching caused by an interaction between two adjacent dyes can be conducted in a homogeneous manner. Therefore, it is an attractive means of detecting or identifying a nucleotide sequence. A homogeneous analytical system is simpler than a conventional method of analyzing hybridization with a probe which is based on detection of fluorescence from a single fluorescent label. This is because a heterogeneous analysis generally requires a further step of separating hybridized labels from free labels which are not hybridized. Typically, the FRET and other related methods are based on monitoring of a change in a fluorescence profile of one (or both) of dye labels upon binding by hybridization of two complementary oligonucleotides. The change in a fluorescence profile is measured as a change in an energy transfer level or a change in a fluorescence quenching level in this system. Typically, it is expressed as an increase in a fluorescence intensity of one of the dyes.

A nucleotide sequence of interest can be detected without separating hybridized oligonucleotides from unhybridized oligonucleotides according to this method. Hybridization can be carried out using two separate complementary oligonucleotides, one labeled with a donor fluorescent substance and another with a quencher.

A nucleotide polymorphism can be identified by using an oligonucleotide having a nucleotide polymorphism-specific sequence as one of the oligonucleotides to provide a polymorphism-specific FRET signal. Several systems for methods of analyzing FRET hybridization are reviewed by Kricka, L. J. (ed.), "Nonisotopic DNA Probe Techniques", Academic Press Inc., pp. 311-352 (1992). Alternatively, one can attach a donor and a quencher to a single oligonucleotide such that the presence and absence of hybridization of the oligonucleotide to a complementary sequence result in a detectable difference in one (or both) of fluorescence profiles. Typically, if an oligonucleotide is hybridized, donor fluorescence is increased and energy transfer/quenching is decreased in this system. For example, if a self-complementary oligonucleotide having labels at both ends forms a hairpin structure, the two fluorescent substances at the 5' end and the 3' end are located in close proximity, resulting in energy transfer and quenching. If the self-complementary oligonucleotide is hybridized to a complementary sequence in a second oligonucleotide, the hairpin structure is destroyed and the distance between the two dyes is increased. Then, the quenching is decreased.

The drawbacks associated with the hairpin structure are as follows. Since the stability is high, conversion to a non-quenching hybridization form is often slow. The performance is generally low with only little inclination towards the non-quenching hybridization form. A hairpin structure labeled as described above that contains a sequence for detection in a loop between self-complementary arms forming a stem is described in Tyagi, S. and Kramer, F. R., Nature Biotechnol., 14:303-308 (1996). The base-paired stem must be melted for hybridization between the sequence for detection and a target which causes decrease in quenching. A "double hairpin" probe and a method of utilizing the same are described in B. Bagwell et al. (Nucleic Acids Res., 22:2424-2425 (1994); U.S. Pat. No. 5,607,834). A target-binding sequence is contained within the hairpin structure. Competitive hybridization participates between the target and a self-complementary sequence in the hairpin structure. Bagwell et al. solve the problem of disadvantageous hybridization kinetics by destabilizing the hairpin structure using a mismatch.

It may be possible to identify a nucleotide polymorphism using this method by selecting a nucleotide polymorphism-specific sequence as a target-binding sequence. It is generally necessary to select stringent hybridization conditions in order to distinguish a difference in a single nucleotide using an oligonucleotide hybridization method.

A homogeneous method in which energy transfer or another fluorescence quenching mode is utilized for detection of nucleic acid amplification has been reported. A real-time detection method in which a doubly labeled detection probe is cleaved in a target amplification-specific manner during a PCR is disclosed in L. G. Lee et al. (Nucleic Acids Res., 21:3761-3766 (1993)). If a detection probe is hybridized to a portion downstream from an amplification primer, the detection probe is digested by a 5'-3' exonuclease activity of Taq polymerase. Then, the two fluorescent dyes forming an energy transfer pair are separated from each other.

It may be also possible to identify a nucleotide polymorphism by using a nucleotide polymorphism-specific probe as a doubly labeled detection probe according to this method.

A method in which detection is carried out using two probes, i.e., a labeled polymorphic site-specific probe and a probe having a donor label which is adjacent to the labeled polymorphic site-specific probe is also known (Reischl, U. et al. (eds.), "Rapid Cycle Real-Time PCR—Methods and Applications, Springer Verlag, pp. 91-96 (2001)). In this case, it is possible to identify a polymorphism by detecting two kinds of FRET signals using the label of the polymorphic site-specific probe and the donor label in combination. According to this method, it is also necessary to select stringent hybridization conditions in order to distinguish a difference in a single nucleotide using an oligonucleotide hybridization method as described above. In addition, four labeled probes are required for the method. An alternative method in which a single labeled polymorphic site-specific probe is hybridized with a donor labeled probe, the temperature is then elevated, and a polymorphism is identified based on the temperature at which the polymorphic site-specific probe is separated into a single strand is known (Bernard, P. S., et al., Anal. Biochem., 255:101-107 (1998)). However, this method requires use of two probes, i.e., a labeled polymorphic site-specific probe and a donor labeled probe, as well as control of dissociation of the donor probe into a single strand.

A method for detecting a target nucleic acid based on FRET between an intercalator as a nucleic acid-specific label and a fluorescent label of a probe hybridized with the target nucleic acid has been disclosed (Heller, "Rapid Detection and Identification of Infectious Agents", Academic Press Inc., pp. 245-256 (1985); Cardullo, R. A. et al., Proc. Natl. Acad. Sci. USA, 85:8790-8794 (1988)); Morrison et al., in Kricka, L. J. (ed.), "Nonisotopic DNA Probe Techniques", Academic Press Inc., Chapter 13 (1992). However, Morrison et al. report that nonspecific binding of an intercalator to portions other than the portion of hybridization with a probe results in increased noise.

A method of detection based on FRET using an intercalator SYBR Green and a probe labeled with a fluorescent label Cy5 has been disclosed (WO 99/28500). However, it has been reported that the use of SYBR Green and Cy5-labeled probe in FRET results in high noise and, therefore, is not suitable for practical use (Cane, P. A. et al., Antimicrob. Agents Chemother., 43:1600-1608 (1999)).

One may consider that a polymorphism can be readily identified by detecting an amplified nucleic acid according to a method as described above. However, the conventional methods have problems for practical use as follows. Since the procedures of the methods are complicated, analyses by obtaining stable signals for a wild type and a polymorphism are made difficult, and a great deal of works are required in order to identify a polymorphism accurately.

For example, in case of electrophoresis, it is necessary to detect a wild type and a polymorphism separately, and it is difficult to numerically express an amount of a nucleic acid based on an electrophoretic image accurately. In case of a Southern blotting method or a sandwich hybridization method, it is necessary to strictly adjust conditions for a hybridization reaction with a probe which is required in the method. In addition, the method requires a step of removing excess probes. Thus, the operation is very complicated.

A method utilizing FRET enables a homogeneous analysis. The detection can be readily carried out because it does not require the removal of excess probes and the like. However, it has been considered doubtful if such a method can be practically used for detection of a genetic polymorphism for the following reasons. The method requires two oligonucleotide probes having different labels, or a doubly labeled probe, specific for each polymorphism. Furthermore, it has been reported that the disclosed method using SYBR Green and a Cy5-labeled probe is not suitable for practical use because of the high noise as described above.

The main object of the present invention is to solve the above-mentioned problems and to provide a method that enables definite and reproducible detection of a polymorphism in a nucleic acid sequence as well as a reagent for the method.

SUMMARY OF THE INVENTION

Under the circumstances, the present inventors studied intensively and found a method superior to the above-identified conventional methods which enable easy and definite identification of a polymorphism without a need of a complicated operation for detection or many expensive labeled probes. According to the method, a labeled oligonucleotide for a wild type or a mutant type is hybridized to a nucleic acid containing a specific nucleotide polymorphic site, a nucleic acid-specific label is allowed to act thereon, an interaction between the label of the oligonucleotide and the nucleic acid-specific label is detected, and a nucleotide polymorphism is identified. A difference due to the nucleotide polymorphism in conditions under which the hybridized oligonucleotide is separated into a single strand is determined in the method. Thus, the present invention has been completed.

Specifically, the present invention is summarized as follows:

(1) a method for identifying a nucleotide polymorphism, the method comprising:

hybridizing a labeled oligonucleotide for a wild type or a mutant type to a nucleic acid containing a specific nucleotide polymorphic site in a sample;

allowing a nucleic acid-specific label to act on the mixture of the oligonucleotide and the nucleic acid;

detecting an interaction between the label of the oligonucleotide and the nucleic acid-specific label; and identifying a nucleotide polymorphism, wherein the identification utilizes a difference due to the nucleotide polymorphism in conditions under which the hybridized oligonucleotide is separated into a single strand;

(2) the method according to (1), wherein the nucleic acid-specific label is a double-stranded nucleic acid-specific label;

(3) the method according to (1) or (2), wherein the nucleic acid-specific label is a fluorescent dye;

(4) the method according to (3), wherein the fluorescent dye as the nucleic acid-specific label has a fluorescence wavelength within a range from 500 to 600 nm;

(5) the method according to any one of (1) to (4), wherein the label of the oligonucleotide is a fluorescent dye;

(6) the method according to (5), wherein the fluorescent dye as the label of the oligonucleotide has an excitation wavelength within a range from 520 to 580 nm;

(7) the method according to (5) or (6), wherein the fluorescent dye as the label of the oligonucleotide has a maximal fluorescence wavelength of 580 nm or more;

(8) the method according to any one of (1) to (7), wherein the interaction is fluorescence resonance energy transfer;

(9) the method according to any one of (1) to (8), wherein the conditions under which the hybridized oligonucleotide is separated into a single strand are temperature conditions;

(10) the method according to any one of (1) to (9), wherein the nucleic acid containing a specific nucleotide polymorphic site in the sample has been amplified beforehand;

(11) the method according to any one of (1) to (9), wherein a reaction mixture containing at least an oligonucleotide for amplification, the labeled oligonucleotide for a wild type or a mutant type, and the nucleic acid-specific label is allowed to act on the nucleic acid containing a specific nucleotide polymorphic site in the sample to conduct an amplification reaction; and the nucleotide polymorphism is identified utilizing the labeled oligonucleotide and the nucleic acid-specific label contained in the reaction mixture;

(12) the method according to (11), wherein the reaction mixture contains a DNA polymerase;

(13) the method according to (12), wherein the DNA polymerase in the reaction mixture has substantially no 5'-3' exonuclease activity;

(14) a method for identifying a nucleotide polymorphism, the method comprising:

hybridizing a labeled oligonucleotide for a wild type or a mutant type to a nucleic acid containing a specific nucleotide polymorphic site in a sample;

allowing a nucleic acid-specific label to act on the mixture of the oligonucleotide and the nucleic acid;

detecting an interaction between the label of the oligonucleotide and the nucleic acid-specific label; and identifying a nucleotide polymorphism, wherein the identification utilizes a difference due to the nucleotide polymorphism in a temperature at which the hybridized oligonucleotide is separated into a single strand upon slow elevation of the temperature of the reaction mixture;

(15) the method according to (14), wherein the nucleic acid-specific label is a double-stranded nucleic acid-specific label;

(16) the method according to (14) or (15), wherein the nucleic acid-specific label is a fluorescent dye;

(17) the method according to (16), wherein the fluorescent dye as the nucleic acid-specific label has a fluorescence wavelength within a range from 500 to 600 nm;

(18) the method according to any one of (14) to (17), wherein the label of the oligonucleotide is a fluorescent dye;

(19) the method according to (18), wherein the fluorescent dye as the label of the oligonucleotide has an excitation wavelength within a range from 520 to 580 nm;

(20) the method according to (18) or (19), wherein the fluorescent dye as the label of the oligonucleotide has a maximal fluorescence wavelength of 580 nm or more;

(21) the method according to any one of (14) to (20), wherein the interaction is fluorescence resonance energy transfer;

(22) the method according to any one of (14) to (21), wherein the nucleic acid containing a specific nucleotide polymorphic site in the sample has been amplified beforehand;

(23) the method according to any one of (14) to (21), wherein a reaction mixture containing at least an oligonucleotide for amplification, the labeled oligonucleotide for a wild type or a mutant type, and the nucleic acid-specific label is allowed to act on the nucleic acid containing a specific nucleotide polymorphic site in the sample to conduct an amplification reaction; and the nucleotide polymorphism is identified utilizing the labeled oligonucleotide and the nucleic acid-specific label contained in the reaction mixture;

(24) the method according to (23), wherein the reaction mixture contains a DNA polymerase;

(25) the method according to (24), wherein the DNA polymerase in the reaction mixture has substantially no 5'-3' exonuclease activity;

(26) a method for identifying a nucleotide polymorphism, the method comprising:

hybridizing an oligonucleotide having a fluorescent label for a wild type or a mutant type to a single-stranded target nucleic acid;

allowing a fluorescent dye as a double-stranded nucleic acid-specific label to act on the mixture of the oligonucleotide and the nucleic acid;

measuring a fluorescence signal resulting from an interaction between the fluorescent dye and the fluorescent label of the oligonucleotide; and determining a temperature at which the oligonucleotide is separated into a single strand upon slow elevation of the temperature of the reaction mixture based on a change in the fluorescence signal measured;

(27) the method according to (26), wherein the fluorescent dye as the double-stranded nucleic acid-specific label has a fluorescence wavelength within a range from 500 to 600 nm;

(28) the method according to (26) or (27), wherein the fluorescent label of the oligonucleotide has an excitation wavelength within a range from 520 to 580 nm;

(29) the method according to any one of (26) to (28), wherein the fluorescent label of the oligonucleotide has a maximal fluorescence wavelength of 580 nm or more;

(30) the method according to any one of (26) to (29), wherein the interaction is fluorescence resonance energy transfer;

(31) the method according to any one of (26) to (30), wherein the nucleic acid containing a specific nucleotide polymorphic site in the sample has been amplified beforehand;

(32) the method according to any one of (26) to (30), wherein a reaction mixture containing at least an oligonucleotide for amplification, the labeled oligonucleotide for a wild type or a mutant type, and the nucleic acid-specific label is allowed to act on the nucleic acid containing a specific nucleotide polymorphic site in the sample to conduct an amplification reaction; and the nucleotide polymorphism is identified utilizing the labeled oligonucleotide and the nucleic acid-specific label contained in the reaction mixture;

(33) the method according to (32), wherein the reaction mixture contains a DNA polymerase; and (34) the method according to (33), wherein the DNA polymerase in the reaction mixture has substantially no 5'-3' exonuclease activity.

DETAILED DESCRIPTION OF THE INVENTION

The present invention will be explained in detail below. There is no specific limitation concerning a nucleic acid (e.g., a chromosome or a fragment thereof) containing a specific nucleotide polymorphic site in a sample as long as it is a target nucleic acid that contains the nucleotide polymorphic site responsible for the information of the gene of interest. Examples of the target nucleic acids include Alu sequences, as well as exons, introns and promoters of protein-encoding genes. Specifically, genes related to various diseases (including genetic diseases), drug metabolism and lifestyle-related diseases (hypertension, diabetes, etc.) exemplify the target nucleic acids. The angiotensin I converting enzyme (ACE) gene exemplifies a gene related to hypertension.

A nucleic acid sequence may be simply referred to as a nucleic acid herein. A mutant type nucleic acid means a nucleic acid in which at least one of nucleotides, preferably a single nucleotide, in a wild type nucleic acid is replaced by another nucleotide as a result of a point mutation, or in which a portion of a wild type nucleic acid contains an inserted or deleted sequence or the like, and of which the site of the mutated nucleotide has been elucidated. Differences in constitutions or the like due to such nucleotide polymorphisms have been elucidated. The method of the present invention is a method for examining whether or not a nucleic acid in a sample has such an expected mutation.

According to the present invention, a reaction of hybridizing an oligonucleotide for a wild type or a mutant type generally comprises allowing the oligonucleotide to act on a target nucleic acid that has been denatured into a single strand to form a double strand.

According to the present invention, an oligonucleotide for a wild type is an oligonucleotide having a sequence complementary to a chromosome or a fragment thereof containing a nucleotide polymorphic site that exhibits a normal phenotype. On the other hand, an oligonucleotide for a mutant type is an oligonucleotide having a sequence complementary to a chromosome or a fragment thereof containing a nucleotide polymorphic site that has a sequence different from a wild type. The length of the oligonucleotide is from 13 to 35 bases, preferably from 16 to 30 bases.

One of the oligonucleotide for a wild type and the oligonucleotide for a mutant type is allowed to act on a sample according to the present invention under conditions under which each oligonucleotide hybridize to both a wild type sequence and a mutant type sequence. For example, if an oligonucleotide of which the 50% melting point is 70° C. is to be allowed to act at 50° C., the oligonucleotide hybridizes to both a wild type sequence and a mutant type sequence with no difference to form double strands. The hybridized oligonucleotide is then subjected to conditions under which the oligonucleotide is separated from a nucleic acid sequence into a single strand. The conditions under which the oligonucleotide is separated into a single strand from a hybrid formed with the wild type sequence are different from those for a hybrid formed with the mutant type sequence. A nucleotide polymorphism can be identified by determining the difference.

Conditions under which an oligonucleotide is separated into a single strand according to the present invention include temperature, pH and electric conditions, but are not limited thereto as long as the conditions can be used to separate a double strand of a nucleic acid into single strands. For example, in case of temperature conditions, an oligonucleotide is separated into a single strand by slowly elevating the temperature after the oligonucleotide is allowed to act on a nucleic acid sequence. In this case, an oligonucleotide for a wild type hybridized with a wild type sequence is separated into a single strand at a temperature higher than the temperature at which the oligonucleotide for a wild type hybridized with a mutant type sequence is separated into a single strand. A nucleotide polymorphism can be identified based on the difference in the temperature.

According to the present invention, a chromosome or a fragment thereof containing a specific nucleotide polymorphic site can be amplified basically using a conventional method. Usually, a region between a forward primer and a reverse primer is amplified using a target nucleic acid as a template by reacting a chromosome or a fragment thereof containing a specific nucleotide polymorphic site that has been denatured into a single strand in the presence of four kinds of deoxynucleoside triphosphates (dNTPs), a DNA polymerase, the forward primer and the reverse primer.

Nucleic acid amplification methods include PCR, NASBA (Nucleic acid sequence-based amplification method; Compton, J., Nature, 350:91 (1991)), LCR (WO 89/12696, JP-A 2-2934), SDA (Strand Displacement Amplification: Walker, G. T. et al., Nucleic Acids Res., 20:1691 (1992)), RCR (WO 90/1069), and TMA (Transcription mediated amplification method; Abe, C. et al., J. Clin. Microbiol., 31:3270 (1993)).

Among these, the PCR method is a method in which a region of a nucleic acid in a sample between a pair of oligonucleotides is exponentially amplified by repeating a cycle consisting of three steps (i.e., denaturation, annealing and extension steps) in the presence of the nucleic acid in the sample, four kinds of deoxynucleoside triphosphates, the pair of oligonucleotides and a thermostable DNA polymerase. Specifically, the nucleic acid in the sample is denatured in the denaturation step; the oligonucleotides are hybridized to regions complementary thereto in the single-stranded nucleic acid in the sample in the annealing step; and DNA strands complementary to the respective single-stranded nucleic acids in the sample as templates are extended from the oligonucleotides by the action of the DNA polymerase in the extension step to produce double-stranded DNAs. One double-stranded DNA is amplified to two double-stranded DNAs in one cycle. Theoretically, the region of the DNA in the sample between the pair of oligonucleotides is amplified $2^n$-fold by repeating this cycle "n" times. Since the amplified DNA region exists in large amounts, it can be readily detected using electrophoresis or the like. Since a gene amplification method can be used to detect a trace amount of a nucleic acid in a sample which could not be detected according to a conventional method (detection of one molecule is possible), it is a technique widely used recently.

A nucleotide polymorphism is identified according to the present invention by amplifying a chromosome or a fragment thereof containing a specific nucleotide polymorphic site using the above-mentioned method, hybridizing a labeled oligonucleotide for a wild type or a mutant type thereto, allowing a nucleic acid-specific label to act thereon, and determining conditions under which the hybridized oligonucleotide is separated into a single strand. All reagents necessary for the reactions may be contained in the reaction mixture. Specifically, a reaction of amplifying a nucleic acid followed by a reaction of detecting a polymorphism can be carried without opening a cap of a reaction vessel after adding a target nucleic acid to a reaction mixture containing a primer for amplification, a polymerase, a labeled probe for detection, a nucleic acid-specific labeling reagent and the like. According to this method, no complicated operation is required for detection, and the risk of contamination with an amplification product, which is associated with a nucleic acid amplification method, can be greatly reduced.

According to the present invention, it is preferable for obtaining reproducible results with low noise that a label of an oligonucleotide has a relative absorption intensity of 0.25 or more, preferably 0.3 or more, more preferably 0.35 or more, most preferably 0.4 or more (defining the intensity at the maximal excitation wavelength as 1) at a wavelength at which a nucleic acid-specific label has a relative fluorescence intensity of 0.3 or more (defining the fluorescence intensity at the maximal fluorescence wavelength for the nucleic acid-specific label as 1).

Specifically, it is preferable that the excitation wavelength of a label of an oligonucleotide is within a range from 520 to 580 nm. Preferably, the label of the oligonucleotide has a relative absorption intensity of 0.05 or more at every wavelength ranging from 520 to 580 nm, and it has a relative absorption intensity of 0.25 or more, preferably 0.3 or more, more preferably 0.35 or more, most preferably 0.4 or more at a wavelength selected from 520 to 580 nm, defining the intensity at the maximal excitation wavelength as 1.

Furthermore, it is preferable that a nucleic acid-specific label has a fluorescence wavelength within a range from 500 to 600 nm. Preferably, the nucleic acid-specific label has a relative fluorescence intensity of 0.5 or more, preferably 0.6 or more, more preferably 0.8 or more at a wavelength selected from 500 to 600 nm, defining the fluorescence intensity at the maximal fluorescence wavelength as 1. More preferably, the nucleic acid-specific label has a maximal fluorescence wavelength within a range from 500 to 600 nm.

It is preferable that the fluorescence wavelength for the nucleic acid-specific label overlaps little with the fluorescence wavelength for the label of the oligonucleotide. Preferably, the relative fluorescence intensity of the nucleic acid-specific label at the fluorescence measurement wavelength for the label of the oligonucleotide is 0.25 or less, preferably 0.2 or less, more preferably 0.15 or less, defining the fluorescence intensity at the maximal fluorescence wavelength for the nucleic acid-specific label as 1.

Preferably, the measurement of fluorescence from the label of the oligonucleotide is carried out at a wavelength that results in a relative fluorescence intensity of 0.5 or more, preferably 0.6 or more, more preferably 0.7 or more, defining the fluorescence intensity at the maximal fluorescence wavelength for the label of the oligonucleotide as 1.

Furthermore, the maximal absorption wavelength for the label of the oligonucleotide is preferably 580 nm or more.

The properties concerning the excitation wavelength and the fluorescence wavelength are those in solutions subjected to actual measurements following amplification.

Any label can be used as a label of an oligonucleotide as long as it fulfills the above-mentioned requirements and it interacts with a nucleic acid-specific label. Examples thereof include ROX, Texas Red, LightCycler RED 640, LightCycler RED 705, TAMRA and Alexa Fluor 633. The label may be attached to an oligonucleotide at any position as long as the attachment does not influence the hybridization of the oligonucleotide. The label is preferably attached at the 5' or 3' end.

Also, any nucleic acid-specific label can be used as long as it fulfills the above-mentioned requirements, specifically binds to a nucleic acid reacted with a labeled oligonucleotide, and interacts with the label of the oligonucleotide. It is preferably a double-stranded nucleic acid-specific label. Double-stranded nucleic acid-specific labels include, but are not limited to, substances that intercalate into double strands such as SYBR Green I, ethidium bromide, acridine orange, thiazole orange, oxazole yellow, rhodamine and Pico Green, with SYBR Green I and Pico Green being preferable.

A combination of the nucleic acid-specific label and the label of the oligonucleotide may be selected according to the above-mentioned criteria. Specifically, an exemplary combination consists of: SYBR Green I and ROX; SYBR Green I and Texas Red; SYBR Green I and LightCycler RED 640; SYBR Green I and LightCycler RED 705; SYBR Green I and TAMRA; SYBR Green I and Alexa Fluor 633; Pico Green and ROX; Pico Green and Texas Red; Pico Green and LightCycler RED 640; Pico Green and LightCycler RED 705; Pico Green and TAMRA; or Pico Green and Alexa Fluor 633. The combination preferably consists of: SYBR Green I and Texas Red; SYBR Green I and LightCycler RED 640; or SYBR Green I and LightCycler RED 705, with the combination of SYBR Green I and Texas Red being more preferable.

Kit

The kits according to the present invention includes a kit of reagents for detection of a nucleotide polymorphism which contains a labeled oligonucleotide for a wild type or a mutant type and a nucleic acid-specific label.

If detection is to be carried out in combination with amplification, the kit may further contain a forward primer, a reverse primer, a DNA polymerase and four kinds of deoxynucleoside triphosphates (dNTPs).

Any DNA polymerase may be used as long as it can be used for extension from a primer and amplification reactions. Preferably, the DNA polymerase contains substantially no 5'-3' exonuclease activity.

EXAMPLES

The following Examples illustrate the present invention in more detail, but are not to be construed to limit the scope thereof.

Example 1

Detection of a Nucleotide Polymorphism of the Endothelial Nitric Oxide Synthase Gene (1) Syntheses of Oligonucleotides for Detecting a Polymorphism at the 298th Position in the Endothelial Nitric Oxide Synthase Gene Oligonucleotide having nucleotide sequences of SEQ ID NOS:1 to 3 (hereinafter referred to as Oligos 1 to 3) were synthesized by DNA synthesis companies (Nippon Bio Service (JBioS), Sawady Technology, Genset KK, Amersham Pharmacia Biotech, etc.) at our requests.

Oligo 1 has a sequence containing "G" at the polymorphic site at the tenth position from the 5' end, and is labeled with Texas Red at the 5' end. It is modified with dideoxy at the 3' end.

(2) Analyses of a Polymorphism of the Endothelial Nitric Oxide Synthase Gene Using Melting Curves (i) Amplification Reactions According to the PCR Method Nucleic acid fragments containing a nucleotide polymorphic site (Glu298Asp; GAG (Glu)→GAT (Asp)) of the human endothelial nitric oxide synthase gene were amplified. The amplification reactions were carried out under the conditions as described below by using, as samples, DNA solutions extracted from human leukocytes according to a phenol/chloroform method and adding the following reagents.

Reagents

A solution of 25 µl containing the following reagents was prepared.

| Taq DNA polymerase reaction mixture: | |
|---|---|
| Oligo 2 | 4 pmol |
| Oligo 3 | 20 pmol |
| ×10 buffer | 2.5 µl |
| 2 mM dNTPs | 2.5 µl |
| 25 mM MgCl$_2$ | 1.5 µl |
| Taq DNA polymerase (Toyobo) | 1 U |
| Extracted DNA solution | 20 ng |

Amplification conditions:
95° C. for 5 minutes; 95° C. for 30 seconds; 60° C. for 30 seconds; 72° C. for 30 seconds (35 cycles); 72° C. for 2 minutes.

(ii) Detection Using Melting Curves

The following reagents (5 µl) were added to 25 µl of each amplification reaction mixture of (i). The mixtures were transferred to capillary reaction vessels for LightCycler (Roche). The capillary reaction mixtures were placed in LightCycler, and melting curves were prepared under the following conditions.

Reagents

A solution of 5 µl containing the following reagents was prepared.

| | |
|---|---|
| 1000-fold diluted SYBR Green I (Molecular Probes) | 1.2 µl |
| 200 mM EDTA (pH 8.0) | 1 µl |
| Oligo 1 | 10 pmol |

Reaction conditions
95° C. for 1 second; 50° C. for 1 minute;

The temperature was elevated from 50° C. to 95° C. at a rate of 0.5° C./second, and the fluorescence was measured with STEP.

Figure 1:
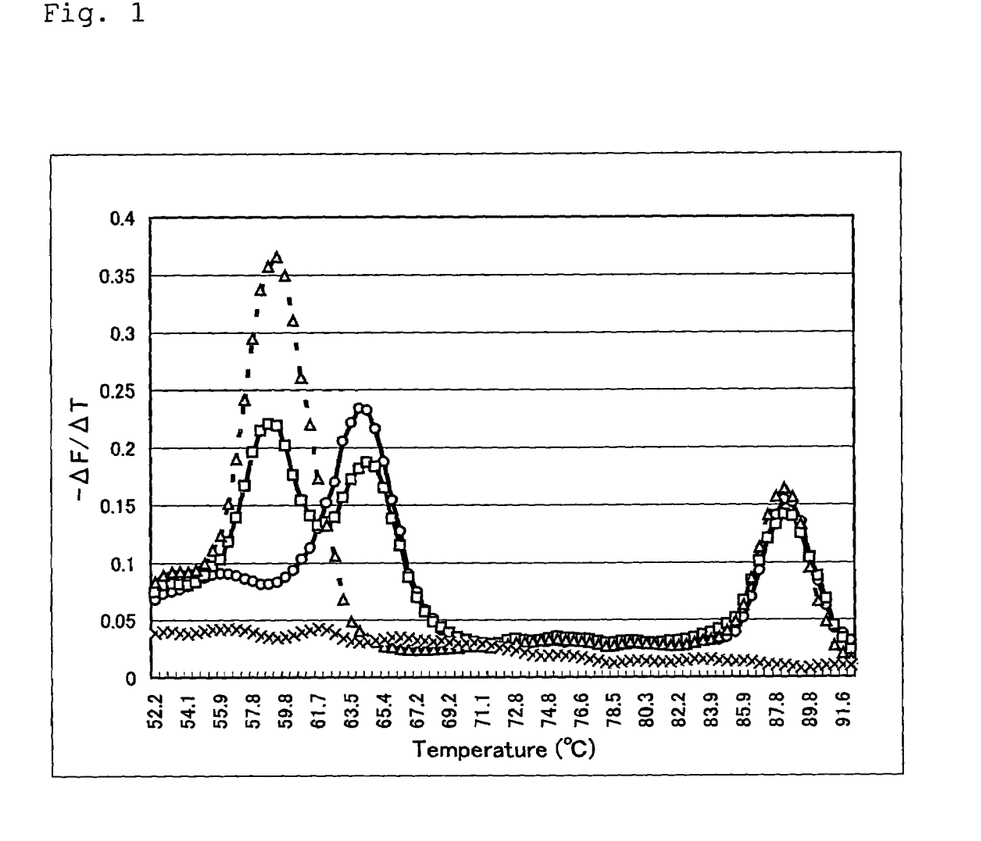
FIG. 1 represents melting curves obtained for analyses of a polymorphism of the endothelial nitric oxide synthase gene in Examples.

The thus obtained melting curves are shown in FIG. 1. In the figure, open circles represent results for a wild type homozygote (G/G), open squares represent results for a heterozygote (G/T), open triangles represent results for a polymorphic homozygote (T/T) and "Xs" represent results for a blank. As seen from the figure, a melting curve having a peak at about 70° C. was obtained in case of a sequence completely complementary to Oligo 1; a melting curve having a peak at about 65° C. was obtained in case of a homozygotic polymorphic sequence; and a melting curve having two peaks at about 65 and 70° C. was obtained in case of a heterozygotic sequence.

The required total time was several minutes.

As described above, a genetic polymorphism in a target nucleic acid could be definitely determined readily and rapidly without a complicated operation by amplifying a nucleic acid fragment containing a sequence of a polymorphic site, hybridizing a labeled oligonucleotide containing the polymorphic site, allowing a nucleic acid-specific label to act thereon, and measuring the temperature at which the labeled oligonucleotide is dissociated into a single strand.

(iii) Analyses of a Polymorphism of the Endothelial Nitric Oxide Synthase Gene Using Real-time Amplification Plus Melting Curves DNA solutions extracted from human leukocytes according to a phenol/chloroform method were used as samples. The following reagents were added thereto. The mixtures were transferred to capillary reaction vessels for LightCycler (Roche). The capillary reaction mixtures were placed in LightCycler. Nucleic acid fragments containing a nucleotide polymorphic site (Glu298Asp) of the human endothelial nitric oxide synthase gene were amplified under the following conditions. Melting curves were then prepared without opening the caps of the reaction vessels using a labeled oligonucleotide probe contained in the reaction mixtures.

Reagents

A solution of 25 µl containing the following reagents was prepared.

| | |
|---|---|
| Oligo 1 | 10 pmol |
| Oligo 2 | 4 pmol |
| Oligo 3 | 20 pmol |
| ×10 buffer | 2.5 µl |

-continued

| | |
|---|---|
| 2 mM dNTPs | 2.5 μl |
| 25 mM MgCl$_2$ | 1.25 μl |
| KOD plus DNA polymerase (Toyobo) | 1 U |
| 3000-fold diluted SYBR Green I (Molecular Probes) | 2.5 μl |
| 2.5 mg/ml BSA | 2.5 μl |
| Extracted DNA solution | 20 ng |

Amplification/detection conditions
Amplification cycle:
95° C. for 1 minute; 95° C. for 1 second; 60° C. for 10 seconds; 72° C. for 3 seconds (40 cycles).
Melting curve cycle:
95° C. for 1 second; 50° C. for 1 minute;

The temperature was elevated from 50° C. to 95° C. at a rate of 0.5° C./second, and the fluorescence was measured with STEP.

Figure 2:
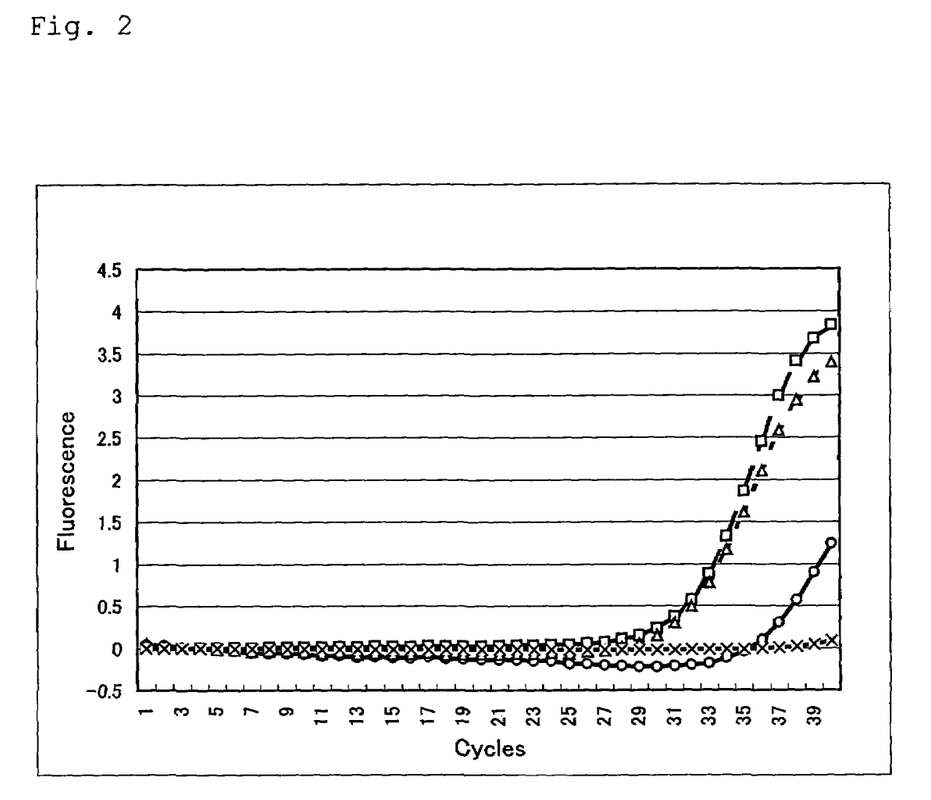
FIG. 2 is a figure illustrating signals for amplification products obtained for analyses of a polymorphism of the endothelial nitric oxide synthase gene in Examples describing real-time amplification.
Figure 3:
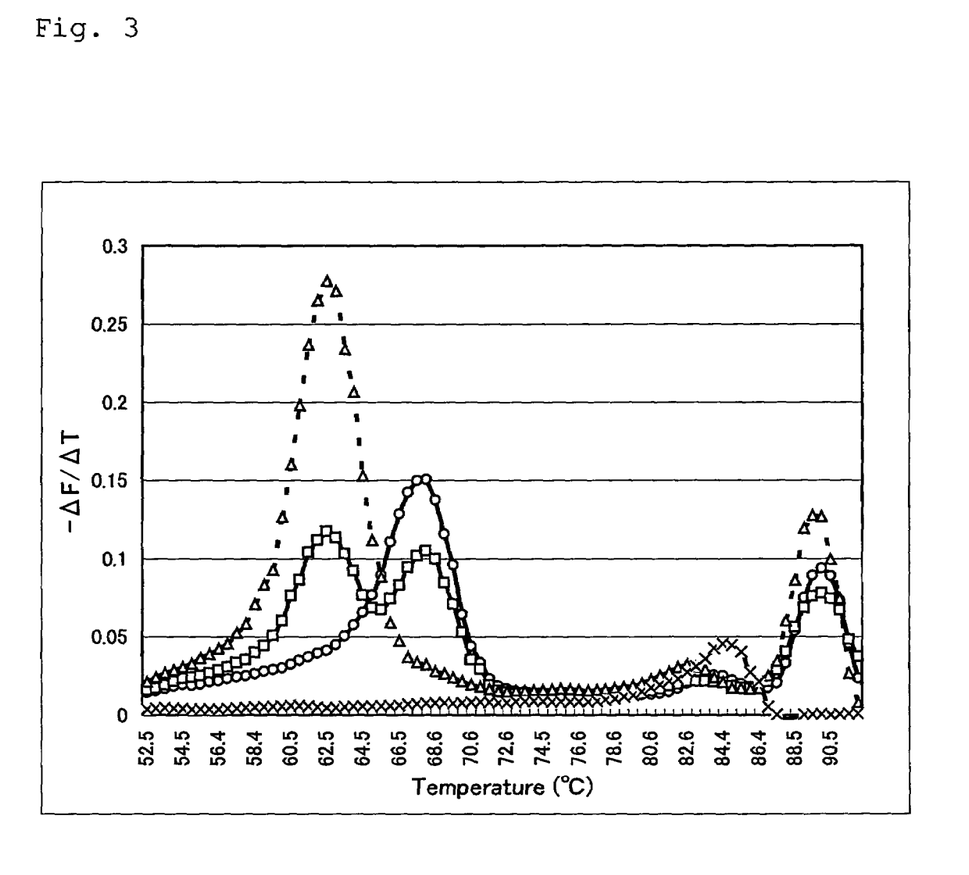
FIG. 3 represents melting curves obtained for analyses of a polymorphism of the endothelial nitric oxide synthase gene in Examples describing real-time amplification.

The thus obtained signals from SYBR Green I for the amplification products are shown in FIG. 2, and the melting curves are shown in FIG. 3. In the figures, open circles represent results for a wild type homozygote (G/G), open squares represent results for a heterozygote (G/T), open triangles represent results for a polymorphic homozygote (T/T) and "Xs" represent results for a blank. As seen from FIG. 2, the amplification could be definitely observed in a real-time manner based on the signals from SYBR Green I. As to the melting curves which were prepared following the measurements of the signals, a melting curve having a peak at about 70° C. was obtained in case of a sequence completely complementary to Oligo 1; a melting curve having a peak at about 65° C. was obtained in case of a homozygotic polymorphic sequence; and a melting curve having two peaks at about 65 and 70° C. was obtained in case of a heterozygotic sequence.

The required total time was about 30 minutes.

The relative absorption intensities at 520 nm, 550 nm and 580 nm for Texas Red were 0.07, 0.31 and 0.63, respectively, defining the absorption intensity at the maximal absorption wavelength as 1. The relative fluorescence intensities at 520 nm, 550 nm and 580 nm for SYBR Green I were 1.00, 0.62 and 0.29, respectively, defining the absorption intensity at the maximal fluorescence wavelength as 1.

SYBR Green I was excited at 495 nm, and the measurement of fluorescence from Texas Red was carried out through a 620-nm filter. In this case, the relative fluorescence intensity for Texas Red was 1, and the relative fluorescence intensity for SYBR Green was 0.13, each defining the absorption intensity at the maximal fluorescence wavelength as 1.

The maximal absorption wavelength for Texas Red is about 590 nm.

Measurements could be carried out similarly using ROX, LightCycler RED 640 or LightCycler RED 705 as a label of an oligonucleotide in place of Texas Red (a 700-nm filter was used for the measurement using LightCycler RED 705).

As described above, a genetic polymorphism in a target nucleic acid could be definitely determined readily and rapidly without a complicated operation and without adding a reaction mixture or opening/closing a reaction vessel. The determination was carried out by amplifying a nucleic acid fragment containing a sequence of a polymorphic site, hybridizing a labeled oligonucleotide containing the polymorphic site, allowing a nucleic acid-specific label to act thereon, and measuring the temperature at which the labeled oligonucleotide is dissociated into a single strand.

Sequence Listing Free Text

SEQ ID NO:1: A synthetic DNA having a sequence containing a nucleotide polymorphic site (Glu298Asp) of the human endothelial nitric oxide synthase gene.

SEQ ID NO:2: A synthetic DNA having a sequence of the human endothelial nitric oxide synthase gene.

SEQ ID NO:3: A synthetic DNA having a sequence complementary to the human endothelial nitric oxide synthase gene.

What is claimed is:

1. A method for identifying a nucleotide polymorphism, the method comprising:
   (a) hybridizing a labeled oligonucleotide to a nucleic acid containing a specific nucleotide polymorphic site in a sample, wherein the oligonucleotide has a sequence complementary to a wild type or mutant sequence at the specific nucleotide polymorphic site in the nucleic acid, wherein the label of the oligonucleotide is Texas Red™ (1H, 5H, 11H, 15H-xantheno[2,3,4-ij:5,6,7-i'j']diquinolizin-18-ium, 9-(2-sulfo-4-chlorosulfonphenyl)-2,3,6,7, 12,13,16,17-octahydro-, inner salt), and wherein the Texas Red™ is attached to the 3' end of the oligonucleotide;
   (b) allowing a nucleic acid-specific label to act on a mixture of the oligonucleotide and the nucleic acid, wherein the nucleic acid-specific label is SYBR™ Green I;
   (c) detecting an interaction between the label of the oligonucleotide and the nucleic acid-specific label, wherein the interaction is fluorescence resonance energy transfer; and
   (d) identifying a nucleotide polymorphism, wherein the identification utilizes a difference due to the nucleotide polymorphism in conditions under which the hybridized oligonucleotide is separated into a single strand, and wherein the identification can distinguish a nucleic acid containing a specific nucleotide polymorphism derived from a heterozygote from a nucleic acid containing a specific nucleotide polymorphism derived from a homozygote.

2. The method according to claim 1, wherein the conditions under which the hybridized oligonucleotide is separated into a single strand are temperature conditions.

3. The method according to claim 1, wherein the method comprises amplifying the nucleic acid containing a specific nucleotide polymorphic site in the sample before step (a).

4. The method according to claim 1, wherein a reaction mixture containing at least an oligonucleotide for amplification, the labeled oligonucleotide, and the nucleic acid-specific label is allowed to act on the nucleic acid containing a specific nucleotide polymorphic site in the sample to conduct an amplification reaction; and the nucleotide polymorphism is identified utilizing the labeled oligonucleotide and the nucleic acid-specific label contained in the reaction mixture.

5. The method according to claim 4, wherein the reaction mixture contains a DNA polymerase.

6. The method according to claim 5, wherein the DNA polymerase in the reaction mixture has substantially no 5'-3' exonuclease activity.

7. The method of claim 2, wherein the interaction between the label of the oligonucleotide and the nucleic acid-specific label is detected in step (c) by measuring a fluorescence signal resulting from the interaction between the SYBR™Green I and the label of the oligonucleotide, and a nucleotide polymorphism is identified in step (d) by determining a temperature at which the oligonucleotide is separated into a single strand upon elevation of the temperature of the reaction mixture based on a change in the fluorescence signal measured.

* * * * *